US011104915B2

(12) United States Patent
Parker et al.

(10) Patent No.: US 11,104,915 B2
(45) Date of Patent: Aug. 31, 2021

(54) VIRAL VECTOR ASSAY AND VECTOR

(71) Applicant: Trizell Ltd., Chinnor (GB)

(72) Inventors: Nigel Parker, Chinnor (GB); Hanna P. Lesch, Kuopio (FI); Jenni Mykkanen, Kuopio (FI); Sara Paulo, Kuopio (FI); Minna Hassinen, Kuopio (FI); Robert Shaw, Kuopio (FI)

(73) Assignee: Trizell Ltd., Chinnor (GB)

( * ) Notice: Subject to any disclaimer, the term of this patent is extended or adjusted under 35 U.S.C. 154(b) by 332 days.

(21) Appl. No.: 15/754,598

(22) PCT Filed: Sep. 9, 2016

(86) PCT No.: PCT/US2016/050959
§ 371 (c)(1),
(2) Date: Feb. 23, 2018

(87) PCT Pub. No.: WO2017/048599
PCT Pub. Date: Mar. 23, 2017

(65) Prior Publication Data
US 2019/0338307 A1 Nov. 7, 2019

Related U.S. Application Data

(60) Provisional application No. 62/218,810, filed on Sep. 15, 2015.

(51) Int. Cl.
*C12N 15/86* (2006.01)
*G01N 33/50* (2006.01)
*G01N 33/569* (2006.01)

(52) U.S. Cl.
CPC ....... *C12N 15/86* (2013.01); *G01N 33/56983* (2013.01); *C12N 2710/10343* (2013.01); *C12N 2710/10351* (2013.01)

(58) Field of Classification Search
None
See application file for complete search history.

(56) References Cited

U.S. PATENT DOCUMENTS

2007/0111296 A1 5/2007 Yin et al.

OTHER PUBLICATIONS

Candolfi et al., Neuro-Oncology, 2007, 9:245-258. (Year: 2007).*
Ayuso, Eduard. "Manufacturing and Characterization of a Recombinant Adeno-Associated Virus Type 8 Reference Standard Material" Human Gene Therapy. Nov. 2014. p. 977-987, V25.
Clement, Nathalie. "Manufacturing of recombinant adeno-associated viral vectors for clinical trials" Molecular Therapy—Methods & Clinical Development. Mar. 2016. p. 1-7.
Dinney, Colin P.N.. "Phase 1 Trial of Intravesical Recombinant Adenovirus-Mediated Interferon-a2b Formulated in Syn3 . . . " Journal Urology. Sep. 2013. p. 850-856, 190(3).
Khabar, Khalid S.A.. "MTS Interferon Assay: A simplified Cellular Dehydrogenase Assay . . . " Journal of Interferon and Cytokine Research. 1996. p. 31-33, V16.
La Rocca, Christopher J.. Oncolytic adenovirus expressing interferon alpha . . . Surgery (author manuscript). May 2015. p. 888-898. 157(5).
Lambright Es. "Inclusion of the herpes symplex thymidine kinase . . . " Gene Therapy. 2001. p. 946-953. V8.
Madigan, Michael T.. Brock Biology of Microorganisms 12th edition. 2008. p. 299, p. 812.
Mcclure, Christina. "Production and Titering of Recombinant Adeno-associated Viral Vectors" Journal of Visualized Experiments. Nov. 2011. p. 1-6, I57.
Murphy, Dano B. "Guidance for Industry Guidance for Human Somatic Cell Therapy and Gene Therapy" Center for Biologics Evaluation and Research. 1998. p. 1-27.
Ramakrishnan, Rupal. "Combined modality immunotherapy and chemotherapy: a new perspective" Cancer Immunology Immunother. Apr. 2008. p. 1523-1529, V57.
Toth, Karoly. "Increasing the Efficacy of Oncolytic Adenovirus Vectors" Viruses. 2010. p. 1844-1866, V2.
Weaver, Linda Shonk. "Evaluation of Adenovirla Vectors by Flow Cytometry" Methods. 2000. p. 297-312, V21.
Westphal, Manfred. "Adenovirus-mediated gene therapy with sitimagene ceradenovec . . . " Lancet Oncology. 2013. p. 823-833, V14.
Vile, Richard G.. "Systemic Gene Therapy of Murine Melanoma Using Tissue Specific . . . " Cancer Research. Dec. 1994. p. 6228-6234, V54.
Zhang, X. "Conditioned medium from Ad-IFN-a-infected bladder cancer and normal urothelial cells . . . " Cancer Gene Therapy. 2008. p. 817-822, V15.
Grigorov, B. et al, Rapid titration of measles and other viruses: optimization with determination of replication cycle length, PLOS One, 6(9): e24135 (2011).
Guidance for Human Somatic Cell Therapy and Gene Therapy, U.S. Department of Health and Human Services Food and Drug Administration Center for Biologies Evaluation and Research, 30 pages (Mar. 1998).
Hubbell, H. R. et al., Independent sensitivity of human tumor cells lines to interferon and double-stranded RNA, 44 Cancer Res., 3252-3257 (1984).
International Search Report for PCT/US2016/050959, 4 pages (dated Feb. 24, 2017).
Pfeffer, L. M. et al., Cytoskeletal Association of Human alpha-interferon receptor complexes in interferon-sensitive and -resistant lymphoblastoid cells, PNAS, 84:3249-3253 (1987).
Written Opinion for PCT/US2016/050959, 8 pages (dated Feb. 2, 2017).

\* cited by examiner

*Primary Examiner* — Stacy B Chen
(74) *Attorney, Agent, or Firm* — Choate, Hall & Stewart LLP; Rolando Medina; Alexandra A. Bouza

(57) ABSTRACT

A process for assaying viral vector manufactured by large-scale viral vector manufacturing processes to assure the resulting vector has acceptable purity and potency. The process entails three different types of assays, each one of which is optionally useful on a stand-alone basis, and which together provide the first system able to assure the quality of viral vector produced by large-scale vector manufacturing processes.

4 Claims, 15 Drawing Sheets

| Plate1 | | | Plate2 | | | Plate3 | | | Plate4 | |
|---|---|---|---|---|---|---|---|---|---|---|
| TS1 30 | TS1 30 | | TS2 30 | TS2 30 | | RS 30 | RS 30 | | FIM | FIM |
| TS1 60 | TS1 60 | | TS2 60 | TS2 60 | | RS 60 | RS 60 | | | |
| TS1 90 | TS1 90 | | TS2 90 | TS2 90 | | RS 90 | RS 90 | | | |

Plate layouts for 6-wells.
Figure 1

Dilution of IFN-α standard

Dilution of samples

|   | 1 | 2 | 3 | 4 | 5 | 6 | 7 | 8 | 9 | 10 | 11 | 12 |
|---|---|---|---|---|---|---|---|---|---|---|---|---|
| A | Std1 | Neat | Neat | Neat | Neat | 800 IU/ml | Std1 | Neat | Neat | Neat | Neat | Neat |
| B | Std2 | 1:2 | 1:2 | 1:2 | 1:2 | 300 IU/ml | Std2 | 1:2 | 1:2 | 1:2 | 1:2 | 1:2 |
| C | Std3 | 1:4 | 1:4 | 1:4 | 1:4 | 100 IU/ml | Std3 | 1:4 | 1:4 | 1:4 | 1:4 | 1:4 |
| D | Std4 | 1:8 | 1:8 | 1:8 | 1:8 | blank | Std4 | 1:8 | 1:8 | 1:8 | 1:8 | 1:8 |
| E | Std5 | Neat | Neat | Neat | Neat | blank | Std5 | Neat | Neat | Neat | Neat | Neat |
| F | Std6 | 1:2 | 1:2 | 1:2 | 1:2 | 800 IU/ml | Std6 | 1:2 | 1:2 | 1:2 | 1:2 | 1:2 |
| G | Std7 | 1:4 | 1:4 | 1:4 | 1:4 | 300 IU/ml | Std7 | 1:4 | 1:4 | 1:4 | 1:4 | 1:4 |
| H | Std8 | 1:8 | 1:8 | 1:8 | 1:8 | 100 IU/ml | Std8 | 1:8 | 1:8 | 1:8 | 1:8 | 1:8 |
|   | Control #1 | Control #2 | Neg Control | Neg cells | QC controls |   | TS1 | TS2 | TS3 | TS4 | TS5 |

Exemplary pipetting chart for ELISA test.

Figure 4.

|   | 1 | 2 | 3 | 4 | 5 | 6 | 7 | 8 | 9 | 10 | 11 | 12 |
|---|---|---|---|---|---|---|---|---|---|----|----|----|
| A | X | X | X | X | X | X | X | X | X | X | X | X |
| B | X | C | C | C | C | C | C | C | C | C | C | X |
| C | X | C | C | C | C | C | C | C | C | C | C | X |
| D | X | C | C | C | C | C | C | C | C | C | C | X |
| E | X | C | C | C | C | C | C | C | C | C | M | X |
| F | X | C | C | C | C | C | C | C | C | C | M | X |
| G | X | C | C | C | C | C | C | C | C | C | M | X |
| H | X | X | X | X | X | X | X | X | X | X | X | X |

C: Cell suspension
M: Media only
X: PBS

Cell plating for potency assay.

Figure 5

|   | 1 | 2 | 3 | 4 | 5 | 6 | 7 | 8 | 9 | 10 | 11 | 12 |
|---|---|---|---|---|---|---|---|---|---|---|---|---|
| A | X | X | X | X | X | X | X | X | X | X | X | X |
| B | X | 940 µl | 648 µl | 648 µl | 648 µl | 648 µl | 648 µl | 648 µl | 648 µl | 648 µl | 648 µl | X |
| C | X | 940 µl | 648 µl | 648 µl | 648 µl | 648 µl | 648 µl | 648 µl | 648 µl | 648 µl | 648 µl | X |
| D | X | 940 µl | 648 µl | 648 µl | 648 µl | 648 µl | 648 µl | 648 µl | 648 µl | 648 µl | 648 µl | X |
| E | X | 940 µl | 648 µl | 648 µl | 648 µl | 648 µl | 648 µl | 648 µl | 648 µl | 648 µl | 648 µl | X |
| F | X | 940 µl | 648 µl | 648 µl | 648 µl | 648 µl | 648 µl | 648 µl | 648 µl | 648 µl | 648 µl | X |
| G | X | 940 µl | 648 µl | 648 µl | 648 µl | 648 µl | 648 µl | 648 µl | 648 µl | 648 µl | 648 µl | X |
| H | X | X | X | X | X | X | X | X | X | X | X | X |

X = empty wells corresponding to PBS wells on the infection plate

Growth media on deep-well plate.

Figure 6

Example of gating with 96-well analysis layout

Example of gating with 96-well analysis layout

Example of gating with 96-well analysis layout

Example of gating with 96-well analysis layout

|  | 30000 ppc | 9487 ppc | 3000 ppc | 945 ppc | 300 ppc | 95 ppc | 30 ppc | 9.5 ppc | 3 ppc |  |  |
|---|---|---|---|---|---|---|---|---|---|---|---|
|  | X | X | X | X | X | X | X | X | X | X | X |
| RS D1 | X | 60 µl | 300 µl | 300 µl | 300 µl | 300 µl | 300 µl | 300 µl | 300 µl | 300 µl | GM | X |
| RS D2 | X | 60 µl | 300 µ | 300 µ | 300 µ | 300 µ | 300 µ | 300 µ | 300 µ | 300 µ | GM | X |
| TS1 D1 | X | 60 µl | 300 µ | 300 µ | 300 µ | 300 µ | 300 µ | 300 µ | 300 µ | 300 µ | GM | X |
| TS1 D2 | X | 60 µl | 300 µ | 300 µ | 300 µ | 300 µ | 300 µ | 300 µ | 300 µ | 300 µ | GM | X |
| TS2 D1 | X | 60 µl | 300 µ | 300 µ | 300 µ | 300 µ | 300 µ | 300 µ | 300 µ | 300 µ | GM | X |
| TS2 D2 | X | 60 µl | 300 µ | 300 µ | 300 µ | 300 µ | 300 µ | 300 µ | 300 µ | 300 µ | GM | X |
|  | X | X | X | X | X | X | X | X | X | X | X |

Pipetting chart for serial virus dilutions on deep well plate.

|   | 2 | 3 | 4 | 5 | 6 | 7 | 8 | 9 | 10 | 11 |   |
|---|---|---|---|---|---|---|---|---|---|---|---|
|   | X | X | X | X | X | X | X | X | X | X | X | X |
| B | X | RS D1 | RS D1 | RS D1 | RS D1 | RS D1 | RS D1 | RS D1 | RS D1 | RS D1 | GM | X |
| C | X | RS D2 | RS D2 | RS D2 | RS D2 | RS D2 | RS D2 | RS D2 | RS D2 | RS D2 | GM | X |
| D | X | TS1 D1 | TS1 D1 | TS1 D1 | TS1 D1 | TS1 D1 | TS1 D1 | TS1 D1 | TS1 D1 | TS1 D1 | GM | X |
| E | X | TS1 D2 | TS1 D2 | TS1 D2 | TS1 D2 | TS1 D2 | TS1 D2 | TS1 D2 | TS1 D2 | TS1 D2 | GM | X |
| F | X | TS2 D1 | TS2 D1 | TS2 D1 | TS2 D1 | TS2 D1 | TS2 D1 | TS2 D1 | TS2 D1 | TS2 D1 | GM | X |
| G | X | TS2 D2 | TS2 D2 | TS2 D2 | TS2 D2 | TS2 D2 | TS2 D2 | TS2 D2 | TS2 D2 | TS2 D2 | GM | X |
|   | X | X | X | X | X | X | X | X | X | X | X | X |

X = PBS

*Infections.*

Figure 9

Example of gating with 6-well analysis layout.

Example of gating with 6-well analysis layout.

Example of gating with 6-well analysis layout.

VIRAL VECTOR ASSAY AND VECTOR

RELATED APPLICATIONS

This application is the National Stage of International Application No. PCT/US2016/050959, filed 9 Sep. 2016 which claims priority from United States provisional patent filing Ser. No. 62/218,810, filed 15 Sep. 2015, incorporated here by reference.

BACKGROUND

Viral vectors hold great therapeutic promise. For example, viral vectors are being investigated for cancer therapy, to replace defective native genes in conditions caused by a defective native gene (e.g., beta-thalassemia, hemophilia) and to improve surgical healing. To date, however, no manufacturer has succeeded in manufacturing a viral vector on a scale adequate to treat more than several hundred patients.

One of the impediments to scaling up vector manufacturing is the difficulty in assuring that vector produced by large-scale manufacturing processes is in fact therapeutically equivalent to that produced by smaller-scale processes and is adequately safe, pure and potent for its intended use.

BRIEF DESCRIPTION

We have developed three ways of assaying viral vector to assure its quality. Each one of these assays is useful on a stand-alone basis. Together, they provide the first system able to assure the quality of viral vector produced by large-scale vector manufacturing processes.

BRIEF DESCRIPTION OF THE DRAWINGS

FIG. 1. Plate layouts for 6-well cell culture plates. (infectivity)

FIG. 4. Exemplary pipetting chart for ELISA test. (expression)

FIG. 5. Cell plating for potency assay. (potency)

FIG. 6. Growth media on deep-well plate. (potency)

FIG. 9. An exemplary infection chart for virus infections on deep well plate. (potency)

DETAILED DESCRIPTION

Figure 2:
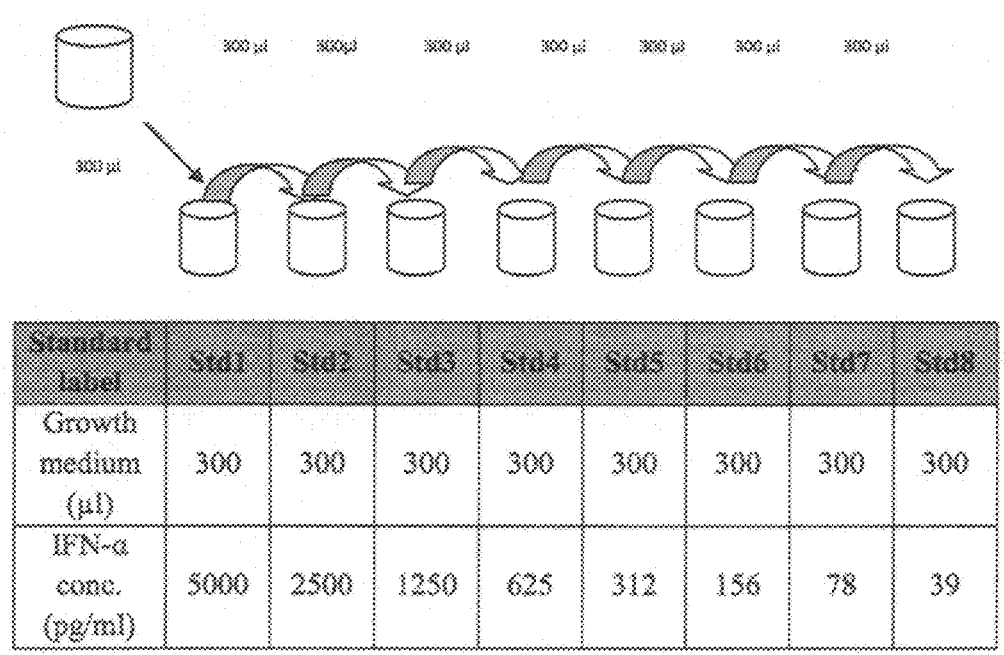
FIG. 2. Dilution of ELISA assay standard. (expression)

Our system entails assaying three different aspects of the viral vector:
1. Virus infectious titer.
2. Expression of the viral transgene (the foreign gene delivered by the viral vector).
3. Potency of the transgene expression product.

Each of these three assays is useful on a stand-alone basis; we discuss each in turn.

1. Virus Infectious Titer

Infection capacity of a viral vector is a key aspect in demonstrating biological activity of the product. Biological activity of the vector is an important factor in determining the correct patient dose, as well as assuring overall efficacy and consistency of the therapy. Our preferred way to measure virus infectious titer is by using flow cytometry analysis. There are other approaches as well.

Example 1: Flow Cytometry Analysis of a Recombinant Viral Vector

We have developed a flow cytometric assay to determine the infectivity of a recombinant viral vector. This assay can be used in conjunction with potency and expression assays for final (commercial) product release to demonstrate the proper biological function of the vector.

In our assay, cells that support adenovirus replication were infected with different concentrations of adenovirus. This is different from the prior art, which teaches to use only one MOI. A single MOI is less expensive to perform and analyze, and may be faster. The art also suggests that multiple MOIs would be useless because the response curve is a threshold value, thus is non-linear. We surprisingly found that by selecting several different suitable virus MOIs, one can produce a linear response curve. A linear response is advantageous because the non-linear (threshold) response curves taught by the prior art fail to provide a clear basis from which one can extrapolate data, and present the risk that an otherwise-minor variation in data can push (or fail to push) the measured results over the threshold, leading to incorrect conclusions.

After infection, we determined the percentage of infected cells with a flow cytometer utilizing a fluorescently conjugated antibody against an adenoviral structural protein. We analyzed samples in parallel with a reference standard and were able to calculate infectivity as relative Infectious Units/ml.

We optimized the assay for cell density upon infection, for virus contact time and for post-infection time. We surprisingly found that cell density was a results-critical variable in this analysis.

We also optimized the staining procedure for flow cytometry.

The prior art teaches to use a Reference Standard merely as an experimental control, to determine whether e.g., the staining in fact was done correctly. In contrast, we prefer to measure results not only from the Test Samples, but also from the Reference Standard(s) and to include those Reference Standard data in our statistical analysis. We find that this improves the reliability of the resulting calculations.

We measured relative infectivity calculated using the Slope Ratio method as outlined in Pharmacopeia Europe 5.3 and United States Pharmacopeia<1034>. We prefer this assay be qualified and validated for International Committee on Harmonization (ICH) Q2 parameters; specificity, linearity, range, accuracy and precision.

This Example provides an example of our performance of an infectivity assay for recombinant Adenovirus bearing an interferon (IFN) transgene ("rAd-IFN"). We here assay rAd-IFN using a fluorescence activated cell sorter (FACS) technique.

Materials and Methods rAd-IFN is a replication deficient recombinant adenovirus type 5 (rAd5)-based interferon alpha-2b (IFNα2b) expression cassette containing gene transfer vector. The assay principle is that HEK293 cells are infected with viral particles and left to produce the virus. We prefer to use a range of viral particles per cell (ppc) and, depending on the viral vector, adjust the infection time and the subsequent incubation/production time (for example, with an adenoviral vector like rAd-IFN, one can infect for about 15 minutes and leave the infected cells to produce the virus for perhaps two days, depending on the temperature, MOI etc. After incubation, cells are fixed and stained with FITC conjugated antibody against adenovirus hexon structural protein. Hexon that has accumulated within infected cells can be quantified with flow cytometer.

All cell work and procedures up to fixing the cells are preferably performed using aseptic techniques in a laminar flow hood. After fixing, the rest of the procedures, before cytometer analysis, are performed in a fume hood. Waste disposal is done according to applicable regulations.

Materials include HEK293 cells and Anti-Adenovirus FITC-labeled Monoclonal Antibody, PBS, TrypLE Select, Cell culture medium, FACS infection medium (FIM), Fixation solution (1:1 Acetone-Methanol) and 30% Bovine Serum Albumin in Phosphate-Buffered Saline; 6-well tissue culture plates, Pipette tips; sterile glass Pasteur pipette; Sterile centrifuge tubes, Sterile centrifuge tubes, Eppendorf tubes, sterile culture tubes, Falcon tubes, Erlenmeyer flasks.

As a control sample, we used rAd-IFN viral vector manufactured by FKD Therapies Oy, Kuopio Finland in a final formulation buffer at a particle concentration of $5.4 \times 10^{11}$ vp/ml, filled as for clinical use. As reference standard, we used purified virus manufactured Merck, Sharpe & Dohme (Switzerland) with a virus particle concentration of $1.4 \times 10^{12}$ vp/ml, infectivity of $1.37 \times 10^{11}$ NAS IU/ml and potency of 251 IU/ml.

Infectivity assay can be run either using 6-well or 96-well plates, depending on the number of samples to be analyzed. Results are reported as a relative titer against the reference standard, and assay performance is monitored using the control sample.

Methods:

On a 6-well plate assay, three test samples (TS), reference standard (RS) and a control sample (CS) can be analyzed. On a 96-well plate 15 test samples can be analyzed. If a comparison between infectivity of different samples needs to be done, the samples should preferably be analyzed in the same assay.

Cell Seeding

HEK293 cells are cultured and their seeding is recorded. Detach and count cells. Prepare a cell suspension that has $7.4 \times 10^5$ cells/ml. The cell count required may be calculated using the formula:

$$\text{Cells} = \frac{(7.4 \times 10^5 \text{cells/ml}) \times 24 \text{ ml}}{\text{cells}/ml \text{ in suspension}}$$

where the volume of medium=24 mL—volume of cell suspension from above.

Pipette the calculated amount of growth medium to a sterile container. Mix cell suspension before transferring the calculated amount of suspension to the container with growth media. Mix the seeding cell suspension. Seed onto 6-well plates. Disperse the cell suspension evenly across the wells. Transfer the seeded plates to a 37° C., 5% $CO_2$ incubator for 22±4 hours.

Infections

On the day of infections, prepare two dilutions (initial dilution (ID) and inoculum) for all samples into pre-warmed FACS infection medium (FIM, PRE-SOL-QC-110). Give calculations to $2^{nd}$ operator for checking before starting the work. Calculate the concentration of the ID using equation:

$$\frac{\frac{vp}{ml} \text{ of } TS \times 0.04 \text{ ml}}{12.04 \text{ ml (total volume of } ID)}$$

Calculate the volume of ID needed for inoculum for using equation:

$$\frac{\left(\text{Final} \frac{vp}{ml} * 10 \text{ ml}\right) vp}{ID \text{ vp/ml} - \text{Final vp/ml}}$$

The final vp/ml on 6-wells is preferably about 60 particles per cell (ppc), or $$60 \text{ vp}*7.4 \times 10^5 \text{ cells}*2 = 8.88 \times 10^7 \text{ vp/ml}$$

Seeded cell number is multiplied by two to get a more accurate estimation of cell number upon infection because HEK293 cells double in approximately 24 hours. (This time thus varies by specific type of cell used). Take the cell plates out of the incubator and inspect cells under a microscope for signs of contamination and record confluence of the cells. Using a sterile glass Pasteur pipettes and a vacuum pump, aspirate media from all wells designated for negative controls (see FIG. 1). Add 1 ml of pre-warmed FIM to the negative control wells. Aspirate medium from RS wells and add 1 ml of ID to each well. Record the time when infections are started. Repeat aspiration and adding virus for all samples. Use FIG. 1 as reference.

Incubate the plates for 15 minutes (±2 min) in 37° C., 5% $CO_2$ incubator. Record the ending time of infections to when first well is aspirated. Aspirate IDs from the cells and add 2 ml of pre-warmed growth media. Incubate the plates for about 2 days at 37° C., 5% $CO_2$ incubator. Record the starting time of incubation.

Removing excess supernatant after centrifugations, especially before fixation, will assure that the cells are aspirated dry.

Label a Falcon tube for each well. Take the plates out from the incubator, note the date and time of removal. Inspect the cells under a microscope and record degree of attachment and confluence. Using a sterile glass Pasteur pipette and a vacuum pump aspirate media from all wells of a sample. Add 0.5 ml of TrypLE express and leave on cells as you move on to the next sample. Change glass Pasteur between samples. Incubate the cells at RT until the cells detach. Add 2 ml of pre-warmed growth media to each well. Ensure cells are in suspension.

Transfer the cells from each tube to a Falcon tube and centrifuge the tubes. Aspirate medium from each tube. Re-suspend the cells in 50-100 µl of supernatant. Add 2 ml of PBS to each tube and mix. Centrifuge. Aspirate supernatant from each tube. Re-suspend the cells in 50-100 µl of supernatant. Add 1 ml of ice cold acetone:methanol to fix the cells and mix so the cells are in single cell suspension.

Incubate the samples at 4° C. to fix them. Add 2 ml of PBS to each tube and mix. Centrifuge to spin down cells. Aspirate supernatant from each tube; re-suspend the cells in 50-100 µl of supernatant. Repeat this washing.

Prepare a 1% BSA in PBS solution by e.g., mixing 1 ml of 30% BSA and 29 ml of PBS. Add 1 ml of 1% BSA in PBS to each tube. Centrifuge. Aspirate supernatant from each tube; re-suspend the cells in 50-100 µl of supernatant.

Add Anti-Hexon antibody to each tube. Stain cells with antibody at +4° C. Add 2 ml of PBS to each tube and mix.

Centrifuge; aspirate supernatant from each tube, re-suspend the cells in 50-100 µl of supernatant. Add 200 µl of PBS to each tube and proceed to FACS analysis.

Flow Cytometer Analysis

FACS CANTO II must be powered on before analysis, and we prefer that CSTbeads are first run as performance check. Run samples using FACSDiva™ software.

We prefer to analyze data using FCS Express™ software. FIG. 7 provides an example of gating.

Replication-Deficient Virus

Titering is a method also applicable to replication deficient virus (e.g., titering of lentiviral or adeno-associated virus). Many viral vectors are by design replication deficient. One may prefer to call transformation by replication-deficient virus "transduction" rather than "infection" (and thus prefer to call the titer of a replication-deficient virus the "transduction titer", and prefer to express the results as "TU/ml" rather than "IU/ml"). The above-described method of measuring titer can equivalently be used to measure titer of a replication-deficient viral vector. For replication-deficient lentivirus, for example, a preferred way to titer is to transduce the host cells and then analyze the transduced cell culture by staining the transgene product. Because replication-deficient and replication-competent viral vector function equivalently in our titration method, in our legal claims we use the word "infect" to encompass transduction" and "infective" to encompass both replication-deficient and replication-competent viral vector.

2. Expression of the Viral Transgene

The second aspect of our assay approach is to measure the expression of the viral transgene by host cells. This may be done by a commercially-available kit, for example the Verikine™ Human IFN-α ELISA kit (commercially available from Pestka Biomedical Laboratories, Piscataway, N.J.). We have found, however, that if one modifies the commercially-available kit by including a more appropriate control and making certain changes to the reaction conditions, the data produced are surprisingly more reliable. We here provide an example of this, measuring the expression of an interferon transgene carried in an adenoviral vector.

Example #2—Expression (Potency) Assay

Introduction

The procedure described in this describes the protocol to measure the capability of recombinant adenoviral vector encoding the human IFNα2b cDNA in an expression cassette that replaces the E1a and pIX regions. Ad-IFN-α expression capability of the virus preparation is determined by transducing UM-UC-3 cells with the recombinant adenoviruses and the concentration of produced IFN-α is measured with IFN-α ELISA.

On day one, $1.5 \times 10^6$ UM-UC-3 cells per well are seeded in volume of 2 ml per well in UM-UC-3 growth medium into 6-well cell culture plates. On the following day cells are transduced with $5 \times 10^5$ particles/ml in UM-UC-3 medium. Day (~24 hours) post infection the medium containing the expressed IFN-αprotein will be collected from the transduced cells. Medium will be centrifuged 209×g for 10 minutes at RT. Diluted samples are analyzed in 96-well plate for IFN-α protein concentration by Verikine™ Human IFN-α ELISA kit (#41100 R & D Systems).

ELISA is an immunological technique, where an antibody or an antigen is measured from a solution by immunologically binding it into a solid phase. An antibody linked with an enzyme then binds to the bound sample. As the substrate solution is added the enzyme changes it into a product that can be measured (e.g., color). The amount of the product is proportional to the amount of the measured sample. To calculate the Reportable Value, interferon samples are titrated against the international standard, the values from the curves can be determined in units/ml (IU/ml) as well as pg/ml. The conversion factor of about 3-5 pg/ml is applicable for human interferon-alpha.

Materials & Methods

UM-UC-3 cells are obtained and expanded into a small cell bank. Interferon alpha-2b is stored at −80° C. as a powder in glass ampoules, about 7 k IU per ampoule. One ampoule at a time is thawed, reconstituted and divided in aliquots. From one ampoule 8-15 aliquots may be obtained. One aliquot is used per assay. A new ampoule is reconstituted as needed.

Purified virus with a virus particle concentration of 1.0 to $1.5 \times 10^{12}$ vp/ml, infectivity of 1 to $2 \times 10^{11}$ NAS IU/ml and potency of 100 to 500 IU/ml, is used as control in assays. Viral particle concentration of release result will be used in calculations for expression. A Control Sample (CS) of purified virus (commercially available from BioCenter Kuopio at A. I. Virtanen Institute for Molecular Sciences, Kuopio Finland) was formulated in 6.25 mMHepes—20% glycerol, at a virus particle concentration of 5 to $10 \times 10^{11}$ vp/ml.

Prepare UM-UC-3 growth medium. Calculate the needed volume of each Test Sample (TS) using total viral particle number result (vp/ml) analyzed for the sample concerned. Target concentration for initial dilution for test samples is $5.4 \times 10^9$ vp/ml. Record calculated concentrations and volumes electronically for each test sample. Calculation formula for the test samples:

$$\text{Volume of neat virus (ml)} = \frac{5.4 \times 10^9 \text{ vp/ml} \times 1 (\text{ml})}{\text{Titer of neat virus (vp/ml)}}$$

Warm the Tryple select and UM-UC-3 culture medium in a +37° C. water bath. Seed cells on six well plates. Prepare duplicate wells for samples and controls (1 sample=10 wells, 2 samples=12 wells, 3 samples=14 wells, 4 samples=16 wells, 5 samples=18 wells).

Detach and count the cells. We prefer that the relative standard deviation for the duplicate cell counts for the cell number is less than about 20% and the cell viability at least about ≥80%. Calculate the volume needed for plates for seeding (we prefer seeding about 1 to $2 \times 10^6$ cells/well. Using 2 ml/well, the total volume of cells needed for one plate is 14 ml (with 2 ml extra). Multiply the volume by a plate number prepared.

$$\frac{14 \text{ ml} \times 7.5 \times 10^5 \text{ cells/ml}}{Cell suspension concentration} = x \text{ ml of cell suspension}$$

Pipette the needed amount of cell culture medium into 50 ml tube (Total volume of cell suspension needed (ml)—X ml of cell suspension). Mix cell suspension thoroughly and transfer the calculated amount of cell suspension into the 50 ml tube. Mix diluted cell suspension and then pipet 2 ml into each well of 6-well plates. Incubate the plate(s) for about one day at +37° C. (±0.5° C.), 5-6% $CO_2$.

Then, prepare Test Samples, Positive Controls (we prefer to use two) and a negative control (we prefer to use vector particles in cell culture medium, for example $5.0 \times 10^5$ particles/ml in UM-UC-3 growth medium; one may, however, use non-transfected host cells in cell culture medium in lieu of or in addition to vector particles). We also prefer to include a negative cell control of growth medium (Table II).

TABLE II

Dilutions of controls and test sample for expression assay.

| Sample | Dilution to be prepared | Dilution used | Volume of sample (µl) | Volume of growth medium (µl) | Titre of dilution (vp/ml) |
|---|---|---|---|---|---|
| Positive Control #1 | 1:100 | Neat | 10 | 990 | $5.0 \times 10^9$ vp/ml |
| | 1:10000 | 1:100 | 10 | 990 | $5.0 \times 10^7$ vp/ml |
| | Infection dilution | 1:10000 | 50 | 4950 | $5.0 \times 10^5$ vp/ml |
| Positive Control #2 | 1:10 | Neat | 10 | 90 | $1.4 \times 10^{11}$ vp/ml |
| | 1:1000 | 1:10 | 10 | 990 | $1.4 \times 10^9$ vp/ml |
| | $5 \times 10^7$ vp/ml | 1:1000 | 50 | 1350 | $5.0 \times 10^7$ vp/ml |
| | Infection dilution | $5 \times 10^7$ vp/ml | 30 | 2970 | $5.0 \times 10^5$ vp/ml |
| Test Sample | Initial dilution | Neat | Calculate with equation in section 4.1 e) | Total volume (1 ml)- sample volume | $5.4 \times 10^9$ |
| | 1:10000 | 1:100 | 10 | 990 | $5.4 \times 10^7$ |
| | Infection dilution | 1:10000 | 30 | 3210 | $5.0 \times 10^5$ vp/ml |
| Negative Control | 1:100 | Neat | 10 | 990 | $3.7 \times 10^9$ |
| | 1:10000 | 1:100 | 10 | 990 | $3.7 \times 10^7$ |
| | Infection dilution | 1:10000 | 30 | 2190 | $5.0 \times 10^5$ vp/ml |

Remove plates from incubator and aspirate the growth media off. Add 0.5 ml of the respective virus dilutions and controls to each well; 2 wells per CS and TS. Add also 0.5 ml to two wells to serve as negative non-infected cells control. Return the plates to the $CO_2$ incubator. Add 2 ml of UM-UC-3 growth media to all wells of the plates and return to the $CO_2$ incubator for about 24 hours.

Then, remove plates from the incubator. For each sample and control, combine the cell supernatants from the replicate wells into a 15 ml centrifuge tube. Centrifuge supernatants to remove any cellular debris. Aliquot the centrifuged supernatants into portions for subsequent ELISA. Label each aliquot with assay running number, date of infection, test sample or control sample identification and store at −80° C.

ELISA Quality control samples (aliquotted) are prepared as follows. Prepare a range of Quality Control sample concentrations (e.g., 800, 300 and 100 IU/ml, or 800, 400 and 200 IU/ml, etc.) in UM-UC-3 growth medium. Label the QC samples with assay running number, QC, CS and concentration. Store in the freezer.

Figure 3:
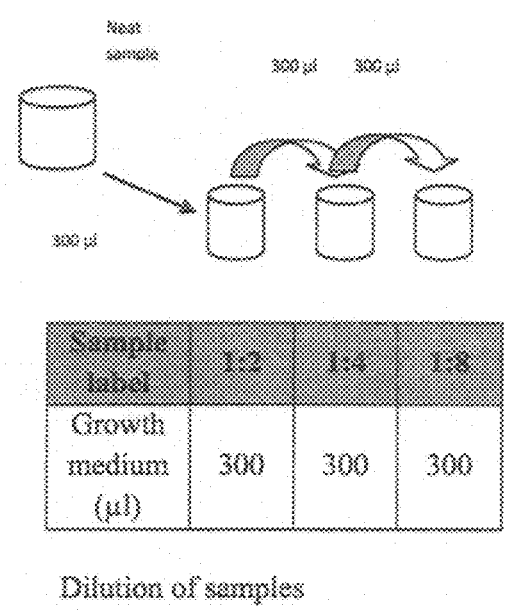
FIG. 3. Dilution of ELISA samples. (expression)
Figure 7A:
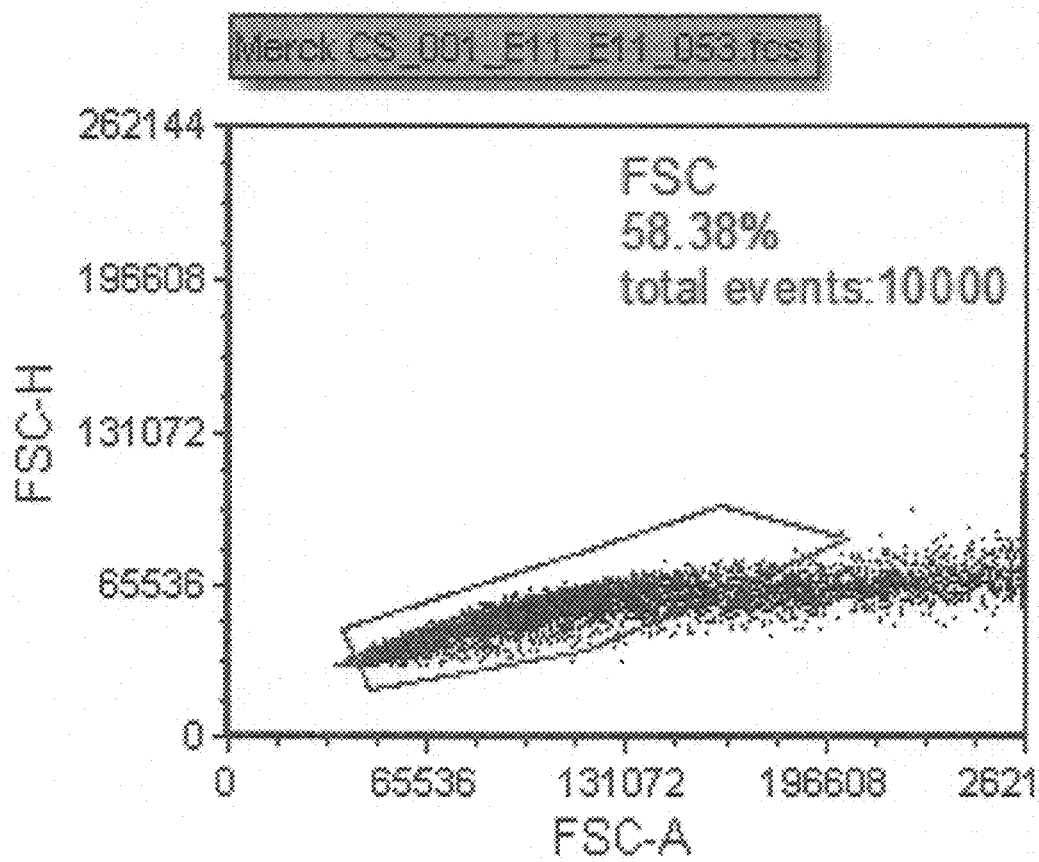
FIG. 7. Example of gating with 96-well analysis layout. (infectivity)
Figure 7B:
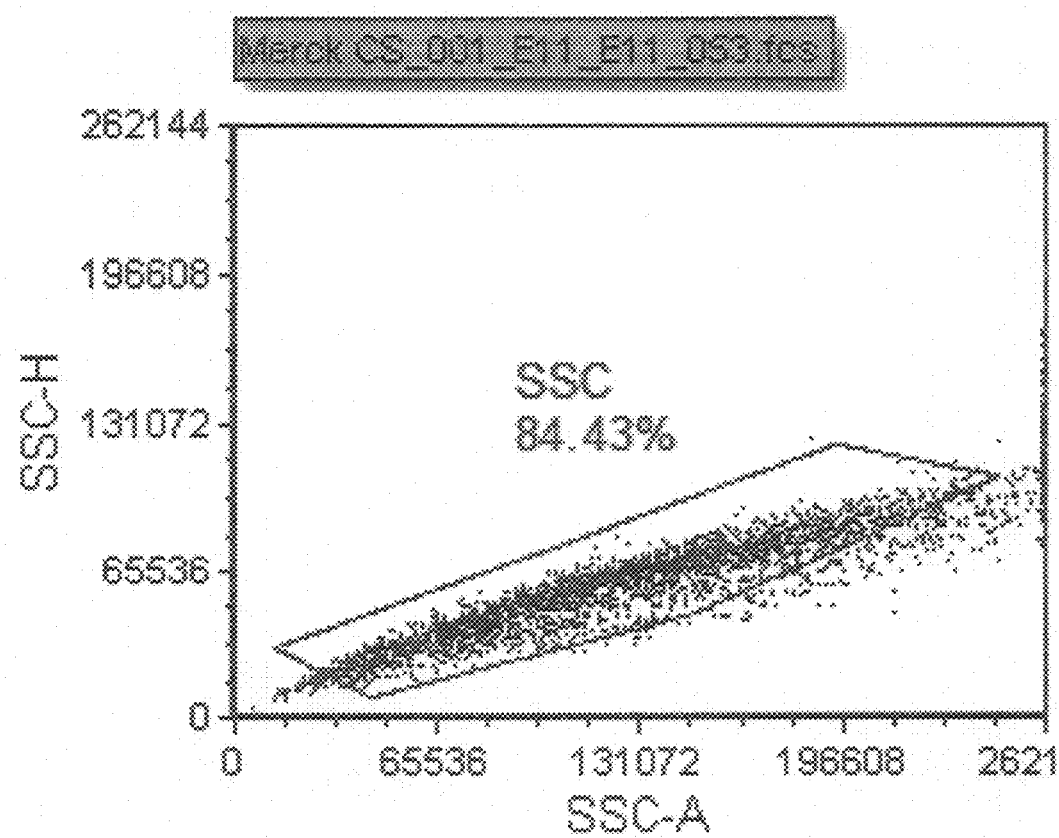
Figure 7C:
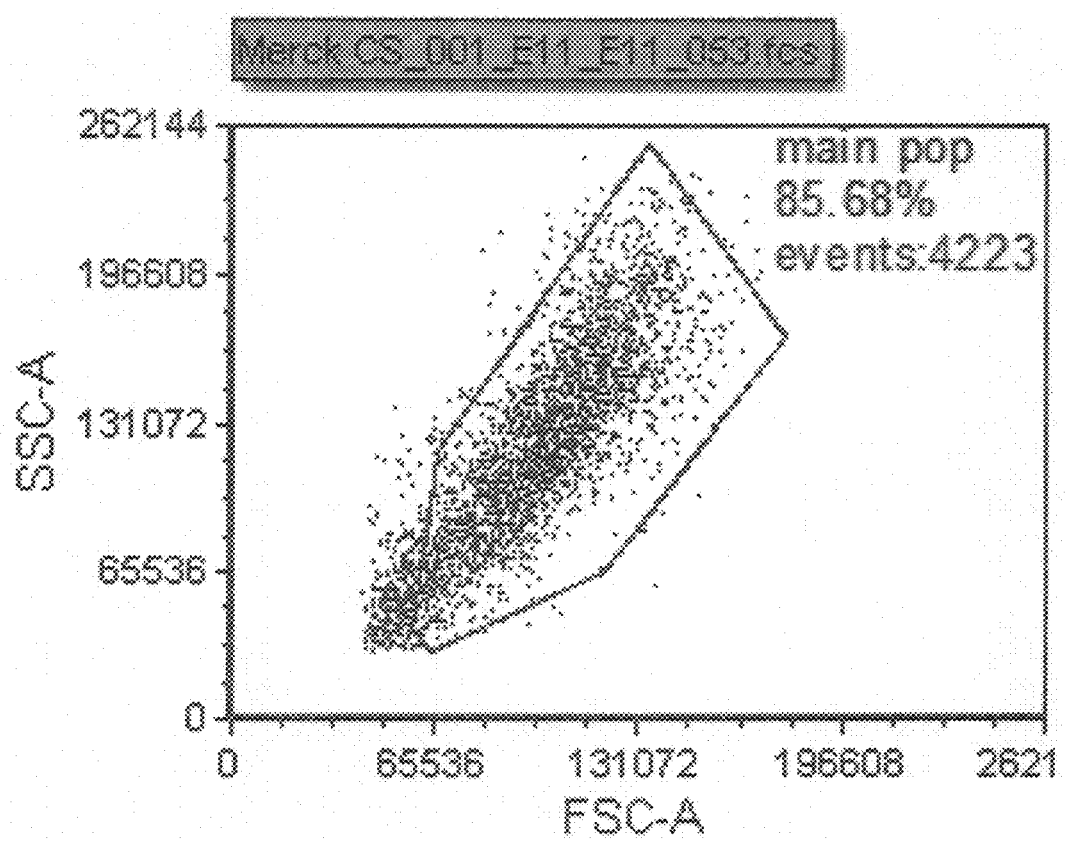
Figure 7D:
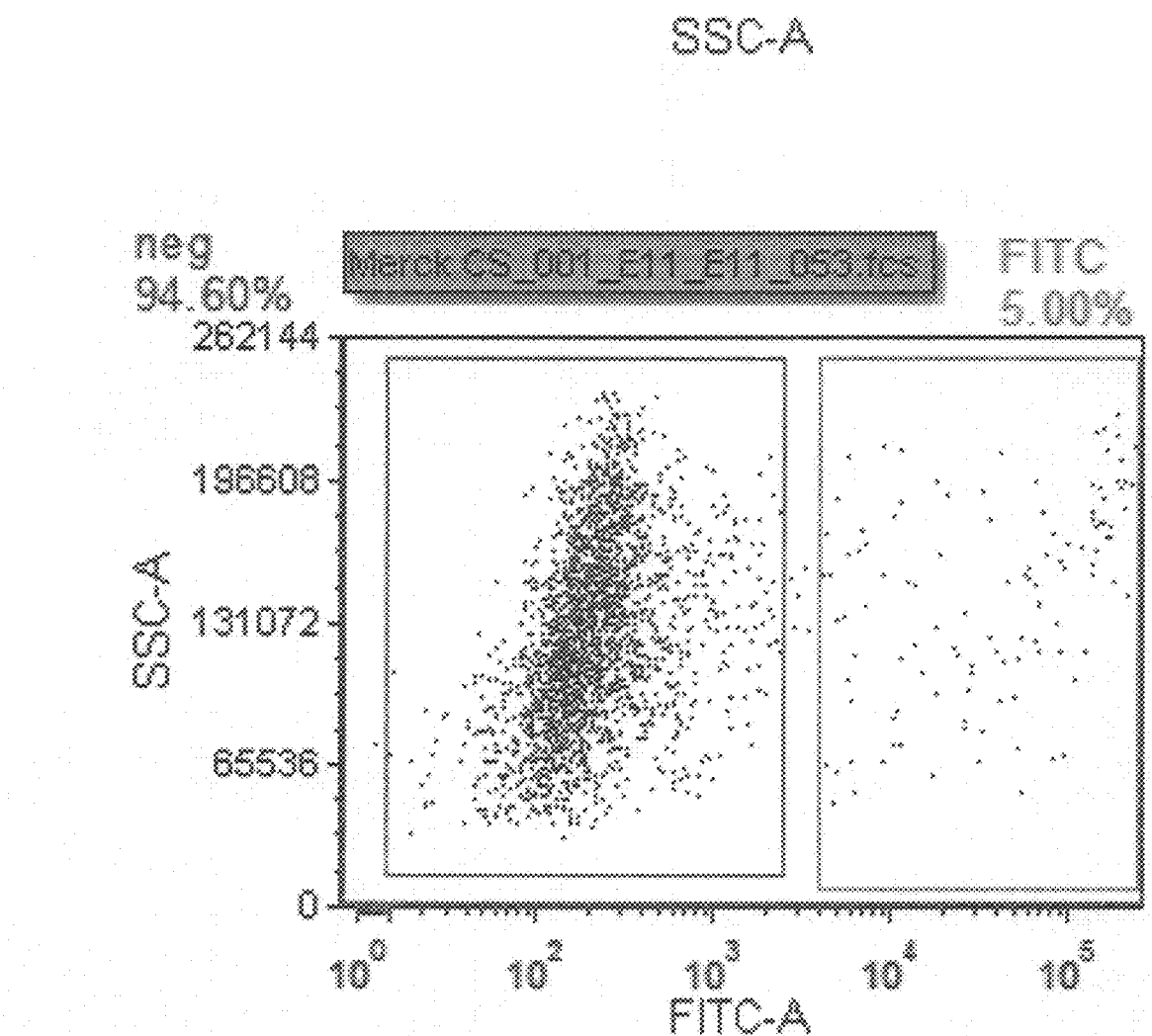

Harvested mediums are analyzed for the presence of INF-α using, for example, Verikine™ Human IFN-α ELISA kit (#41100 R & D Systems). Before starting the ELISA, prepare a wash buffer. One may prepare the standards according to FIG. 2 using serial dilution into UM-UC-3 cell culture medium (RT). One may dilute the test and control samples into UM-UC-3 culture medium according to FIG. 3. One may pipette 125 µl of standards, controls and test samples into V-bottomed 96-well plate according to pipetting chart in FIG. 4. There can be a maximum of 5 test samples in one plate. If fewer TS are used, strips for other samples can be left out from the assay.

Transfer standards, controls and samples from V-bottomed plate to IFN-α antibody coated plate with eight channel pipette. Cover with plate seal provided in the kit and incubate. Dilute the antibody solution according to lot specific specification. After incubation, wash the plate using the microplate washer. Aspirate each well and wash thoroughly with Wash Buffer. After the wash, invert the plate and blot it against a Technicloth.

Add diluted antibody to each well. Cover with plate seal provided in the kit and incubate. Dilute HRP solution with concentrate diluent according to lot specific specification. After incubation, wash the plate. Aspirate each well and wash thoroughly with Wash Buffer. After the last wash, invert the plate and blot it against Technicloth. Add diluted HRP to each well. Cover with plate seal and incubate.

During incubation, warm the 3,3',5,5'-Tetramethylbenzidine (TMB) substrate solution to room temperature. After incubation, wash the plate using the microplate washer. Aspirate each well and wash with Wash Buffer. After the wash, invert the plate and blot it against Technicloth. Add 100 µl of the TMB substrate solution to each well incubate for 15 minutes, After the incubation of TMB, add 100 µl of stop solution.

Measure the absorbance with e.g., a SpectraMax Plus 384 spectrophotometer at 450 nm soon after the addition of the stop solution. Softmax Pro™ software can calculate the concentration of each sample from standard curve using a 4 PL fit for the standard curve.

Results, Analysis and Conclusions

Where a process error is known to have occurred, e.g., a pipetting error or equipment failure, we exclude that replicate value, and make notation describing the error, and recalculate the curve.

To assure adequate quality, we prefer that all standard curve points back calculate to within 25% of their nominal value. If this is not the case, we allow for up to 30% of the individual standard points to be excluded in order to bring all standard points within 25% of their nominal values. Note that the exclusion of a single point may be sufficient to bring other standard curve points within 25% of their nominal value; therefore, it may not be necessary to drop all standard curve points that did not back calculate to within 25% of their nominal value. If standard curve points are excluded, recalculate the curve and attach the original data with an explanation for excluding the data.

We prefer that the $R^2$ value for the curve must be ≥0.99. If greater than 30% of the individual standard curve points are >25% of their nominal values or if $R^2$ is <0.99, we consider the assay invalid or inconclusive and the assay must be repeated.

An assay day is considered valid if the values for ⅔ of the QC samples are within 30% of their nominal value. Use only those values for QC sample whose replicate wells agree with a Coefficient of Variation (CV) percentage of ≤30%. Reporting the mean value for each QC sample, the CV of the mean values must be ≤30%. If less than ⅔ of the QC are within 30% of their nominal values or have a CV >30%, we consider the assay to be inconclusive and the samples must be repeated. For the QC control sample the nominal value is value calculated by dividing pg/ml result by 3.

When determining assay results, we prefer to include only those values which fall on the linear portion of the dose response curve; any value flagged by an "R" we consider outside the standard range and should not be included in final calculations. We prefer to use only those values for sample whose replicate wells agree with a CV of ≤30%. Report the mean value for each sample. The CV of the mean values must be ≤30%. Any sample not meeting this criteria should be repeated.

Values with sample dilutions with obvious matrix effects may be excluded and the means of the other dilutions used as long as they agree with CV of ≤30%. If the only value generated for a sample is greater than the highest point on the linear portion of the standard curve, one may dilute the sample to bring the determination within range and re-assay.

Both positive control samples must be positive for the presence of the transgene expression product, and the negative control and growth medium control must be negative for the presence of it. If these criteria are not met, we consider that the assay is inconclusive and must be repeated.

Reportable value is expressed as IU/ml value as well as pg/ml value. For example, according to the manufacturer of a commercially-available ELISA kit for human interferon alpha, the ELISA is based on the international reference standard for human interferon alpha provided by the National Institutes of Health. Therefore the values from the curves can be determined in units/ml as well as pg/ml. According to the manual accompanying the commercially-available kit, the conversion factor of about 3-5 pg/unit is applicable for human interferon alpha. Result obtained from kit is expressed as pg/ml. Result as IU/ml are calculated by dividing the pg/ml result by 3 and 5. These results may be calculated automatically using a Spectramax™ protocol.

3. Potency of the Transgene Expression Product

A third aspect of our assay system entails assaying the potency of the transgene expression product. Potency assays are one of the key assays in defining the quality of viral vector products. Potency assay measures the therapeutic activity of the viral vector in a biological system. For interferon and similar expression products, we prefer to do this by measuring Expression-Product Mediated Cytotoxicity.

Example 3: Cytotoxic Potency Assay for Recombinant Adenoviral Interferon

Introduction rAd-IFN is recombinant adenoviral gene therapy vector encoding IFNα2b gene. Used to treat, for example, refractory non-muscle invasive bladder cancer, the adenovirus vector transduces bladder wall cells, which in turn express the IFNα2b transgene, which in turn leads to death of cancer cells.

We have developed a relative potency assay measuring the killing efficacy of rAd-IFN. Assay development was started by selection of interferon sensitive human bladder cancer cell lines, preparation of cell bank(s) and proofing the concept of the assay. Interferon-sensitive cells may be purchased commercially from several sources, or may be readily prepared or isolated as is well known in the art. See e.g., Howard R. Hubbell et al., *Independent sensitivity of Human Tumor Cell Lines To Interferon and Double-Stranded RNA*, 44 Cancer Res., 3252 (1984); Lawrence M. Pfeffer et al., *Cytoskeletal Association of Human α-Interferon Receptor Complexes In Interferon-Sensitive and-Resistant Lymphoblastoid Cells*, 84 P.N.A.S. 3249, 3249 col. 1 (1987). Cells were transduced using multiple dilutions of reference standard and test samples leading to expression of IFNα2b and subsequent cell death. We found that cell killing efficiency can, somewhat surprisingly, be determined using a colorimetric method, measuring the dehydrogenase activity of the living cells. The relative potency of a test sample can readily be determined against reference standard response curve after testing parallelism by an equivalence test.

We optimized the assay for cell number, sample dilutions, curve fit, post-infection time and incubation time for colorimetric method. An equivalence test was set up to measure parallelism of test sample and reference standard response curves. Assay qualification and robustness studies are ongoing aiming to qualify the assay for relative accuracy, precision, specificity, linearity and range according to ICH Q2 (R1).

rAd-IFN is a replication deficient recombinant adenovirus type 5 (Ad5) based gene transfer vector containing human interferon alpha-2b (IFNα2b) gene in expression cassette that replaces the E1a, E1b and pIX regions at the 5' end of adenovirus genome. The vector has been developed for intravesical treatment of non-muscle invasive bladder cancer. At the moment, a Phase III clinical trial is being planned.

Potency assay for rAd-IFN determines the vectors cell killing efficacy in an IFN sensitive cell line. For the experiments described here, we used human bladder papilloma cell line RT4. Equivalent interferon-sensitive cells may be purchased commercially from several sources, or may be readily prepared or isolated as is well known in the art. See e.g., Howard R. Hubbell et al., *Independent sensitivity of Human Tumor Cell Lines To Interferon and Double-Stranded RNA*, 44 Cancer Res., 3252 (1984); Lawrence M. Pfeffer et al., *Cytoskeletal Association of Human α-Interferon Receptor Complexes In Interferon-Sensitive and-Resistant Lymphoblastoid Cells*, 84 P.N.A.S. 3249, 3249 col. 1 (1987). For small scale laboratory work, purchasing cells is easy, while for larger-scale and commercial work, isolating cells may prove more cost-effective. In the assay interferon-resistant cells are infected by multiple doses of rAd-IFN. 120 h post infection viability of infected cells is measured by cell counting kit-8 (CCK-8™ kit, commercially available from Dojindo Molecular Technologies).

A standard assay is carried out in four 96-well plates with identical layout, which contain dilution series from the RS as well as one or two TS, blank wells with only growth medium and wells containing only cells. All RS or TS dilutions are applied as duplicates per plate. Three wells per plate containing only growth medium are used for background subtraction and three wells contain only cells for maximum viability determination.

A 4-parameter logistic curve fit is applied to absorbance vs. virus concentration data and after statistical analysis by SAS and R software, a relative potency result is given. Relative potency is the difference in curve midpoints between reference and test sample, after both curves have been determined to be parallel to each other.

Materials & Methods

Interferon-resistant human cells (here, bladder papilloma cells) were thawed. Equivalents may be used. We prefer that the cells be in exponential growth phase when starting the assay (i.e., with a confluency of from about 60% to about 90%) and viability of the cells should be ≥90%.

As a reference Standard, we used a viral vector manufactured by Wehterstein Biopharma (WAG), made with a virus particle concentration of about 1 to $2 \times 10^{12}$ vp/ml, infectivity of about 1 to $5 \times 10^{11}$ NASIU/ml and expression of from about 100 to about 300 IU/ml. We assign an artificial potency value for this in house reference standard of 1 U/vp.

Methods

For preliminary preparations, cells are cultured before starting the potency assay. Obtain the vp/ml results from $OD_{260}$- or HPLC-analysis for test samples that are analyzed and calculate the virus dilutions used in the assay. Total viral particle number results with three significant numbers from $OD_{260}$-measurement or HPLC are needed for calculations. Calculate the needed amount of TS and GM with the formulas below, and round the TS volume to nearest microliter. If the volume is less than 10 µl, first dilute TS e.g., 1:10, or adjust the volume of initial dilution to e.g., 1000 µl instead of 400 µl. Formulas for calculating dilutions for TSs are the following:

$$\frac{\frac{5*10^{10} vp}{ml} * 400 \; \mu l}{TS \; vp/ml} = x \; \mu l \; of \; TS \; needed$$

$$400 \; \mu l - x \; \mu l = volume \; of \; GM$$

Where, 400 µl=total volume of initial dilution and $5 \times 10^{10}$=concentration of initial dilution.

Seeding Plates

Clean a laminar flow hood (LFH). Collect all needed materials into the LFH. Detach and count the cells. Cells must fulfill the following criteria before plating on 96-well plate: Cells are in exponential growth phase; confluence is 60-90%; Cell viability is ≥90%; Passage number is 188-212; and RSD % between cell numbers needs to be ≤20%. Calculate the needed amount of cell suspension for four 96-well plates.

$$\frac{10 \times 10^4 \; cells/ml * 30 \; ml}{number \; of \; cells \; available} = x \; ml \; of \; cell \; suspension$$

$$30 \; ml - x \; ml = needed \; amount \; of \; GM$$

A total of 30 ml of cell suspension with 100,000 cells/ml is needed for four plates. This gives 10,000 cells per well, when 100 µl is seeded on each well. Pipette needed amount of warm growth media (GM) to a 50 ml tube. Mix cell suspension thoroughly. Transfer x ml of cell suspension to the 50 ml tube. To diminish edge effect on the plate, we prefer to pipette PBS to the outermost wells of the 96-well plates. Pipette GM to wells E11-G11, see for example an exemplary pipetting chart in FIG. 5.

For efficiency, one may handle two plates at a time. First mix the cell suspension well. Transfer the suspension to a reagent reservoir. Seed 100 µl per well starting from row B and continuing to row G with a multichannel pipette. See pipetting chart in 5. (Do not seed cells to GM-only wells.) Transfer the seeded plates to $CO_2$-incubator. Incubate cells in $CO_2$-incubator (+37° C., 5% $CO_2$) for about 24 h. Do not stack the plates Infection with Viral Vector Thaw Test Samples (TS) and Reference Standard (RS). Prepare initial dilutions from RS and TS as duplicates in Eppendorf tubes using calculated amounts of virus and GM. Pipette pre-warmed GM to deep well plate.

Figure 8:
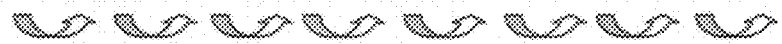
FIG. 8. An exemplary pipetting chart for serial virus dilutions on deep well plate. (potency)
Figure 10A:
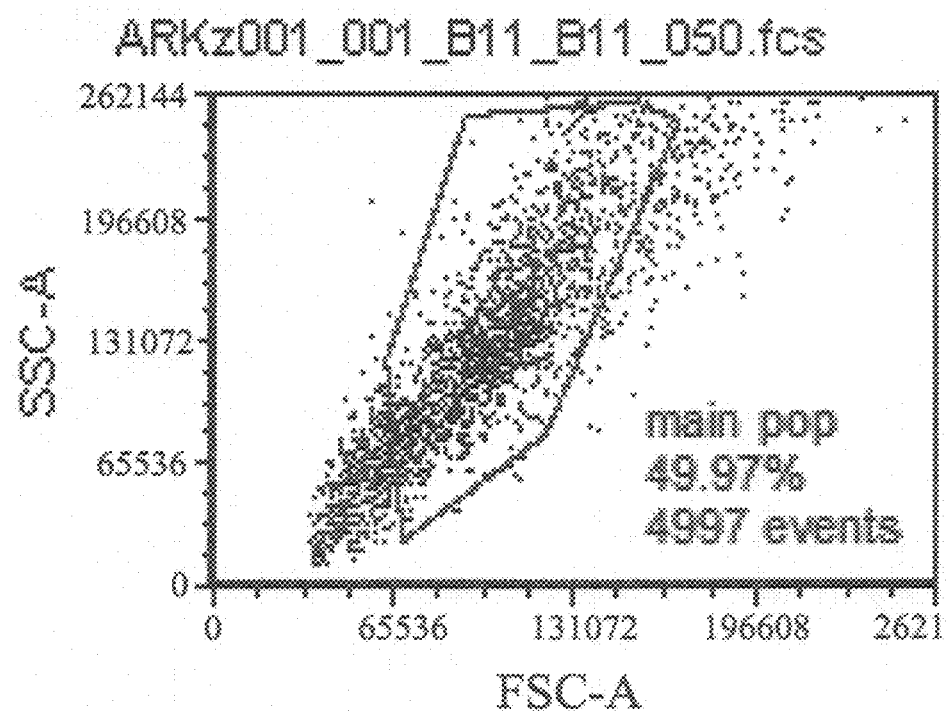
FIG. 10. Example of gating with 6-well analysis layout. (infectivity)
Figure 10B:
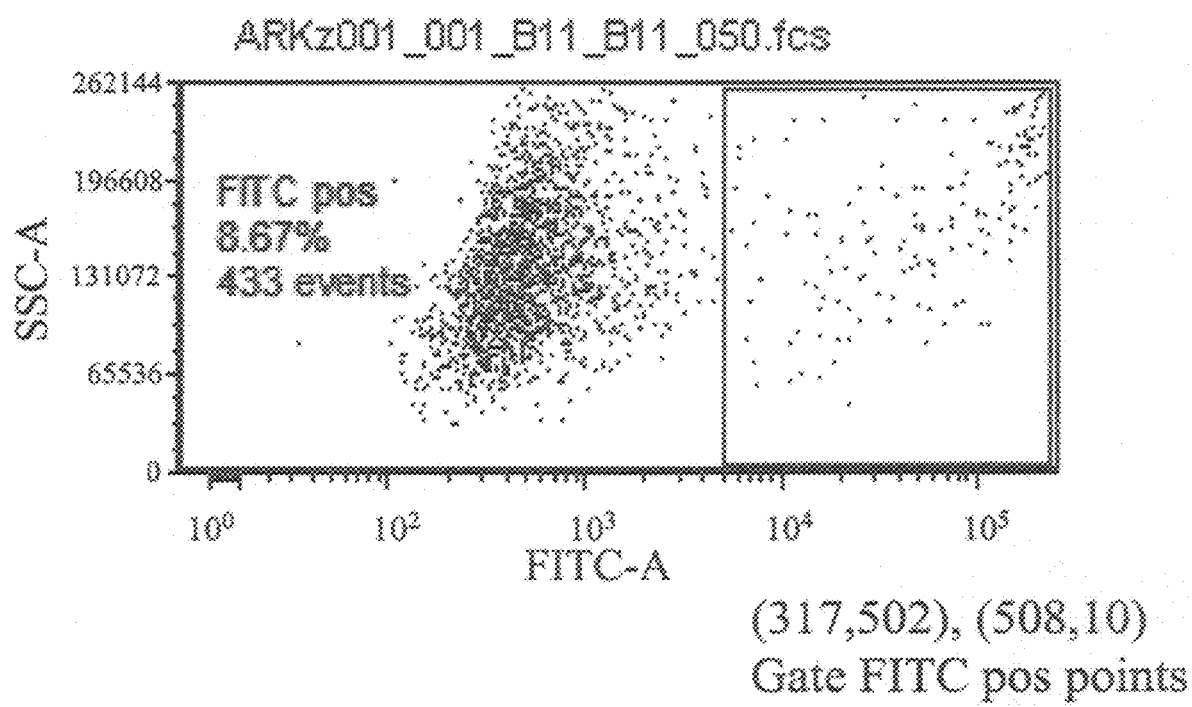
Figure 10C:
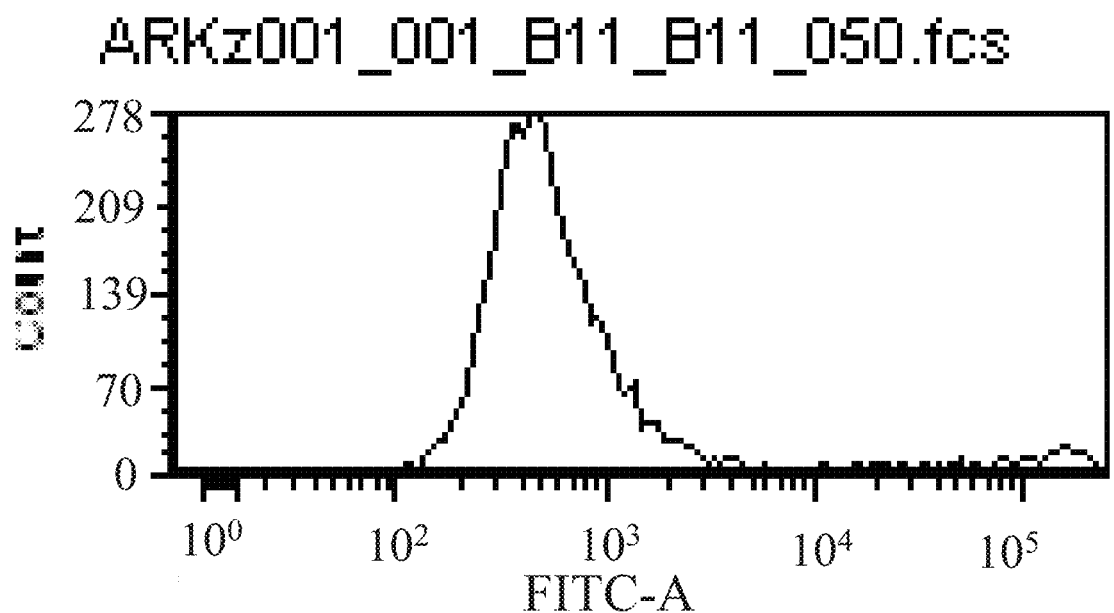

Pipette 60 µl from each initial dilution to column 2 of the deep well plate as instructed in FIG. 8. Mix well. Start serial dilutions by pipetting 300 µl from column 2 to column 3 of the deep well plate. The same pipette tips are used for mixing the more concentrated column and for transferring. New tips are taken before mixing the more dilute column. Continue transferring from one column to the next in this manner, mixing well before each transfer. Mix the last dilution column (10) as well. Do not transfer virus dilutions to the last column (11), which is for cells only and blank wells. See FIG. 8 for an exemplary pipetting chart/map.

Take two cell plates from the incubator to the LFH at a time. Start from plate 1. Remove GM from the plate with a multi-channel pipette starting from row B and continuing to row G. The same pipette tips can be used for the whole plate.

Transfer 100 µl from the deep well plate row B to cell plate row B with a multi-channel pipette. Continue in the same manner pipetting from the deep well plate to the cell plate row by row. See exemplary pipetting chart in FIG. 9. Repeat for additional plate(s) and put all plates to incubator. Incubate the cells for about 120 h in a $CO_2$-incubator (+37° C., 5% $CO_2$). Do not stack the plates.

Measuring Cell Viability

Remove infected plates from the incubator. Remove GM from the plates. Dilute CCK-8 imaging dye 1:10 in warm GM. Mix well and pour dye in a reagent reservoir. Transfer 100 µl of diluted CCK-8 to each well with a multi-channel pipette. Incubate the plates for about 1 h in a $CO_2$-incubator (+37° C., 5% $CO_2$). Do not stack the plates.

Remove plates from the incubator; put each plate in a spectrophotometer microplate reader and press Read. Absorbance is measured at 450 nm and 660 nm.

Analysis

Trend parameters of the assay. We prefer that the following parameters are trended: Parameters A, B, C and D from SpectraMax curve fits for RS; Average $OD_{450}$—values for cells only wells from each plate; and CCK-8 kit lot. The artisan may use others.

Measured absorbance values are statistically analyzed using SAS software, where test sample curves are compared to reference standard curves, their parallelism is assessed and final relative potency values calculated.

We prefer that the assay SSC achieve the following parameters: Viability of interferon-resistant cells before seeding on 96-well plates on day 1 is ≥90%; Passage number of the cells is 188-212 before plating; Confluency of cells is 60-90% before plating; SPECTRAtest plate result is passed; Average $OD_{450}$ of 3 cells only—wells is between 1.078-0.645; and the correlation coefficient ($r^2$) for the 4PL curve fit of the RS as determined by the Molecular Devices software is ≥0.90. (System Suitability Criteria (SSC) concerns each plate individually, so if one plate has SSC-failure only that plate is rejected).

We prefer the following SSC are used to assess the test sample curve in each plate relative to the RS curve in the same plate: the correlation coefficient ($r^2$) for the 4PL curve fit of the TS as determined by the Molecular Devices software is ≥0.90; TS has not failed parallelism testing with slope or upper asymptote (If a TS fails on one plate, that plate is discarded from the assay. If more than one plate fails, the TS fails and needs to be repeated.); and if one plate fails a SSC, RV can be based on 3 plates if the ½ width of 95% CI for the RV of the TS is ≤0.3 logs.

If the SSC fail on one plate, this plate is excluded from analysis. At least 3 plates have to meet the SSC, and if more than one plate fails, the assay is repeated.

4. Summary and Conclusions

Our work enables, for the first time, the artisan to have a method for assaying a viral vector comprising: a. Measuring infectious titer; b. Measuring expression of the viral transgene; and c. Measuring potency of the transgene expression product. Our work similarly enables, for the first time, the artisan to have a method for assaying a viral vector comprising measuring viral vector titer by using more than one MOI. Our work further enables, for the first time, the artisan to have a method for assaying a viral vector comprising measuring viral vector titer by using a cell density of about what we used. Our work furthermore enables, for the first time, the artisan to have a method for assaying a viral vector comprising measuring transgene expression by using a positive control. Our work enables, for the first time, the artisan to have a method for assaying a viral vector comprising measuring vector potency using a colorimetric assay.

The invention claimed is:

1. A process for manufacturing a viral vector having an expressible transgene that can express a polypeptide that has biological activity, comprising: obtaining a sample of the viral vector having the expressible transgene that can express the polypeptide that has biological activity, and then
    assaying said sample by a. measuring viral vector infectious titer by calculating a linear response curve to measure relative infectivity using the Slope Ratio method; and using at least two assays selected from the group consisting of:
    b. measuring transgene expression,
    c. measuring the activity of the polypeptide expressed by said transgene, and
    d. measuring viral particle titer.

2. The process of claim 1, wherein said assaying said sample comprises a. measuring viral vector infectious titer by calculating a linear response curve to measure relative infectivity using the Slope Ratio method, b. measuring transgene expression and c. measuring the activity of the polypeptide expressed by said transgene.

3. The process of claim 1, wherein said assaying said sample comprises d. measuring viral particle titer.

4. The process of claim 1, wherein said assaying said sample comprises: a. measuring viral vector infectious titer, b. measuring transgene expression, c. measuring the activity of the polypeptide expressed by said transgene, and d. measuring viral particle titer.

* * * * *

UNITED STATES PATENT AND TRADEMARK OFFICE
CERTIFICATE OF CORRECTION

PATENT NO. : 11,104,915 B2
APPLICATION NO. : 15/754598
DATED : August 31, 2021
INVENTOR(S) : Parker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 367 days.

Signed and Sealed this
Thirty-first Day of January, 2023

Katherine Kelly Vidal
*Director of the United States Patent and Trademark Office*